United States Patent
Brimhall

[19]

[11] Patent Number: 5,935,110
[45] Date of Patent: *Aug. 10, 1999

[54] CONTROL FORWARD/FLASHBACK FORWARD ONE HAND INTRODUCER NEEDLE AND CATHETER ASSEMBLY

[75] Inventor: Greg L. Brimhall, West Jordan, Utah

[73] Assignee: Becton Dickinson and Company, Franklin Lakes, N.J.

[ * ] Notice: This patent is subject to a terminal disclaimer.

[21] Appl. No.: 08/898,328

[22] Filed: Jul. 22, 1997

Related U.S. Application Data

[63] Continuation of application No. 08/405,324, Mar. 16, 1995, Pat. No. 5,697,914.

[51] Int. Cl.⁶ ............................................. A61M 5/178
[52] U.S. Cl. .................. 604/167; 604/164; 604/264; 604/272; 604/158
[58] Field of Search ..................... 604/161, 164, 604/165, 167, 168, 239, 264, 272, 273, 166, 158, 177, 174

[56] References Cited

U.S. PATENT DOCUMENTS

| | | | |
|---|---|---|---|
| 3,046,984 | 7/1962 | Eby | 128/214 |
| 3,547,119 | 12/1970 | Hall et al. | 128/214.4 |
| 3,589,361 | 6/1971 | Loper et al. | 128/214.4 |
| 3,853,127 | 12/1974 | Spademan | 128/214.4 |
| 4,099,528 | 7/1978 | Sorenson et al. | 128/214.4 |
| 4,149,539 | 4/1979 | Cianci | 128/325 |
| 4,317,445 | 3/1982 | Robinson | 128/214.4 |
| 4,324,236 | 4/1982 | Gordon et al. | 128/214.4 R |
| 4,326,519 | 4/1982 | D'Alo et al. | 128/214.4 |
| 4,353,369 | 10/1982 | Muetterties | 128/214.4 |
| 4,362,156 | 12/1982 | Feller, Jr. et al. | 604/165 |
| 4,419,094 | 12/1983 | Patel | 604/93 |
| 4,496,348 | 1/1985 | Genese et al. | 604/167 |
| 4,531,935 | 7/1985 | Berryessa | 604/45 |
| 4,531,937 | 7/1985 | Yates | 604/53 |
| 4,813,939 | 3/1989 | Marcus | 604/177 |
| 4,834,708 | 5/1989 | Pillari | 604/165 |
| 4,894,052 | 1/1990 | Crawford | 604/63 |
| 4,966,586 | 10/1990 | Vaillancourt | 604/164 |
| 5,059,186 | 10/1991 | Yamamoto et al. | 604/280 |
| 5,084,023 | 1/1992 | Lemieux | 604/167 |
| 5,176,662 | 1/1993 | Bartholomew et al. | 604/283 |
| 5,242,411 | 9/1993 | Yamamoto et al. | 604/167 |
| 5,254,097 | 10/1993 | Schock et al. | 604/167 |
| 5,267,971 | 12/1993 | Brimhall | 604/177 |
| 5,269,764 | 12/1993 | Vetter et al. | 604/167 |
| 5,273,546 | 12/1993 | McLaughlin et al. | 604/167 |
| 5,304,144 | 4/1994 | Brumhall | 604/177 |
| 5,306,243 | 4/1994 | Bonaldo | 604/86 |
| 5,312,359 | 5/1994 | Wallace | 604/164 |
| 5,514,109 | 5/1996 | Mollenauer et al. | 604/249 |
| 5,549,576 | 8/1996 | Patterson et al. | 604/247 |

FOREIGN PATENT DOCUMENTS

| | | |
|---|---|---|
| 2088215 | 6/1982 | United Kingdom . |
| WO 94/23784 | 10/1994 | WIPO . |

*Primary Examiner*—Corrine McDermott
*Assistant Examiner*—Cris L. Rodriguez
*Attorney, Agent, or Firm*—Eric M. Lee

[57] ABSTRACT

The catheter includes a catheter hub at its proximal end having a radially extending wing. The needle is connected at its proximal end to a needle hub. The needle may have at least one notch therein. The needle hub defines a radially extending fin thereon. When the introducer needle is inserted through the catheter such that the distal tip of the needle extends beyond the distal tip of the catheter, the fin on the needle hub extends beyond the distal end of the wing on the catheter hub. This arrangement allows the distal tip of the needle to be retracted into the catheter with a simple proximal motion by the healthcare worker.

1 Claim, 8 Drawing Sheets

CONTROL FORWARD/FLASHBACK FORWARD ONE HAND INTRODUCER NEEDLE AND CATHETER ASSEMBLY

This is a continuation of application Ser. No. 08/405,324, filed Mar. 16, 1995. now U.S. Pat. No. 5,697,914

BACKGROUND OF THE INVENTION

This invention relates to a catheter and introducer needle assembly. Catheters, particularly intravenous (IV) catheters, are used for directing fluid into or withdrawing fluid from a patient. The most common type of IV catheter is an over-the-needle IV catheter. As its name implies, an over-the-needle IV catheter is mounted over an introducer needle having a sharp distal tip. With the distal tip of the introducer needle extending beyond the distal tip of the IV catheter, the assembly is inserted through the patient's skin into a vein. Once placement of the assembly in the vein is verified by flashback of blood in the needle, the needle is withdrawn leaving the IV catheter in place. The proximal end of the IV catheter typically has a hub that is designed to be connectable to an IV fluid supply line after insertion of the IV catheter in a patient.

Although typical IV catheter and introducer needle assemblies generally perform their functions satisfactorily, they do have certain drawbacks. For example, the entire procedure of properly placing an IV catheter into a patient can be cumbersome and awkward and require the use of both hands of the healthcare worker. In addition, prior IV catheter and introducer needle assemblies require a flashback chamber located on the proximal end of the needle. This location is inconvenient for the healthcare worker because during insertion of the assembly into a patient, the healthcare worker's attention is directed to the distal tip of the needle. Thus in order to determine if the needle is properly placed in a vein, the healthcare worker has to divert his attention away from the point of insertion of the IV catheter and introducer needle assembly into the patient. Furthermore, prior IV catheter and introducer needle assemblies do not provide a simple means of breaking adhesion between the needle and IV catheter prior to insertion of the assembly into the patient. Adhesion can occur because the inside diameter of the catheter is typically less than the outer diameter of the needle to provide a smaller profile for the assembly and facilitate insertion of the IV catheter into the patient. Thus, when the assembly is sterilized and is not used for a period of time after sterilization, the catheter can adhere to the introducer needle. In addition, the lubricant that is used on the introducer needle and catheter can contribute to tip adhesion. Finally, prior IV catheter and introducer needle assemblies do not allow for the flexibility of allowing an IV fluid supply line to be connected to the IV catheter prior to insertion of the IV catheter and introducer needle assembly into a patient.

SUMMARY OF THE INVENTION

It is therefore an object of this invention to provide an IV catheter and introducer needle assembly that is easy to control and insert into a patient.

It is another object of this invention to provide an IV catheter and introducer needle assembly that allows the healthcare worker to determine if the assembly is properly placed in a patient's vein without the need for the healthcare worker to divert his attention away from the insertion site.

It is yet a further object of this invention to provide an IV catheter and introducer needle assembly that allows an IV fluid supply line to be connected to the IV catheter prior to insertion of the assembly into a patient.

It is still a further object of this invention to provide an IV catheter and introducer needle assembly that allows adhesion between the IV catheter and the needle to be broken prior to insertion of the assembly into a patient.

It is yet another object of this invention to provide an IV catheter and introducer needle assembly that allows the healthcare worker to withdraw the needle into the IV catheter by using only one hand.

The above and other objects are satisfied by the IV catheter and introducer needle assembly of this invention. The IV catheter includes a hub at its proximal end having a wing radially extending from the IV catheter hub. This catheter wing is generally aligned with the longitudinal axis of the catheter. The IV catheter hub has a side part in fluid communication with the IV catheter. The side port is preferably located distal of the catheter wing. The needle is connected at its proximal end to a needle hub and has a pair of notches formed therein. The notches are formed in the needle such that blood can flow from the needle tip inside the needle through the notches outside the needle into the catheter lumen and through the side port into a translucent extension tube that extends along the distal end of the catheter wing. In this way, the healthcare worker can visualize flashback of blood when the needle has been inserted into a patient's vein.

The needle hub has a radially extending fin formed thereon and is generally aligned with the longitudinal axis of the needle. The needle fin and catheter wing are arranged so that they can rotate with respect to one another. This allows the needle to rotate with respect to the catheter to break any adhesion therebetween. In addition, the needle fin extends forward of the catheter wing when the needle hub is fully engaged with the IV catheter hub. This arrangement allows the distal tip of the needle to be retracted into the catheter with a simple proximal motion by the healthcare worker on the needle fin.

BRIEF DESCRIPTION OF THE DRAWINGS

The above and other objects and advantages will be apparent upon consideration of the following drawings and detailed description. The preferred embodiments of the present invention are illustrated in the appended drawings in which like reference numbers refer to like elements and in which.

DETAILED DESCRIPTION OF THE INVENTION

Figure 1:
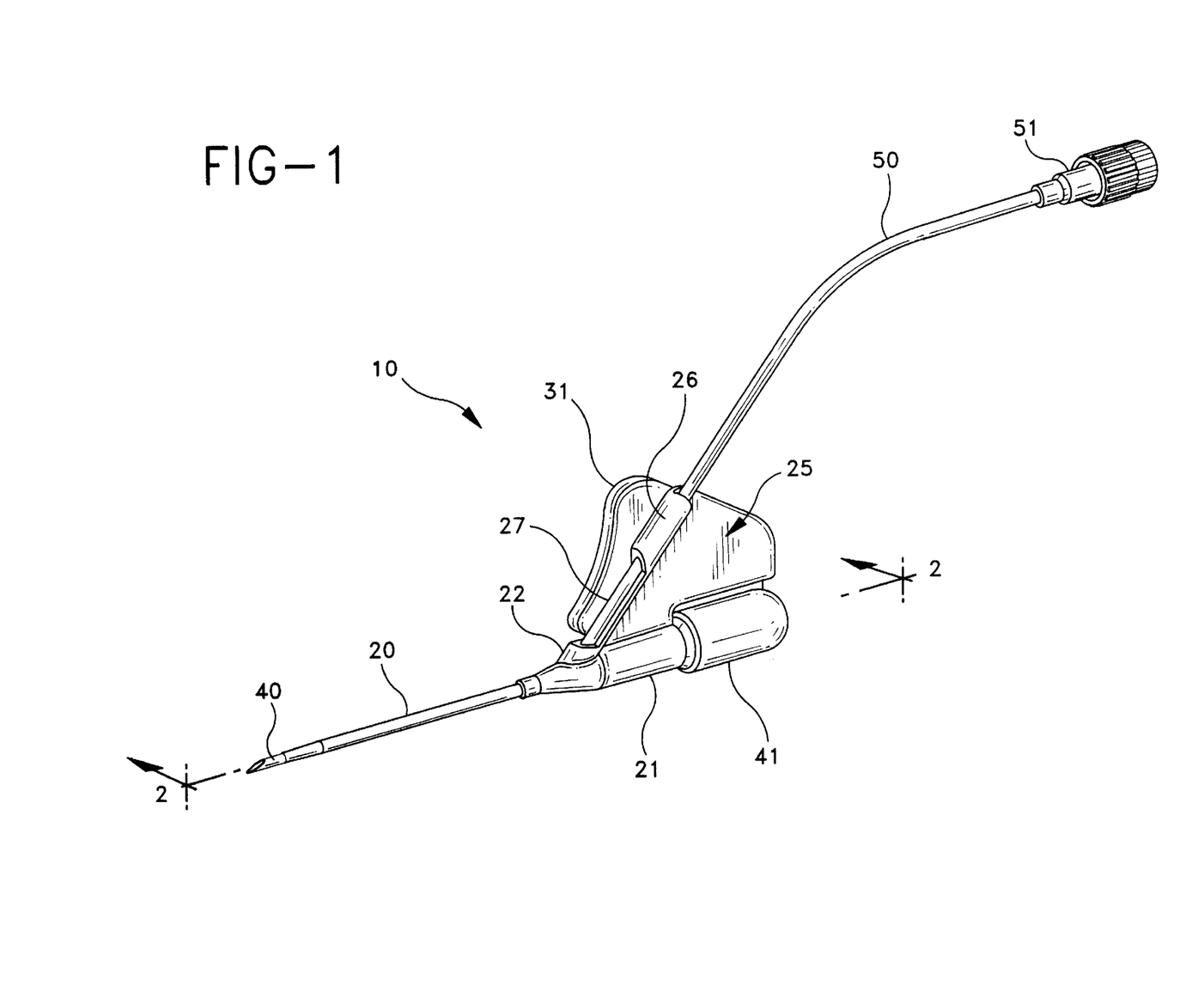
FIG. 1 is a left perspective view of the IV catheter and introducer needle of this invention.

The catheter and introducer needle assembly 10 of this invention is shown in FIG. 1. This assembly includes catheter 20 affixed to catheter hub 21 and needle 40 affixed to needle hub 41.

Figure 4:
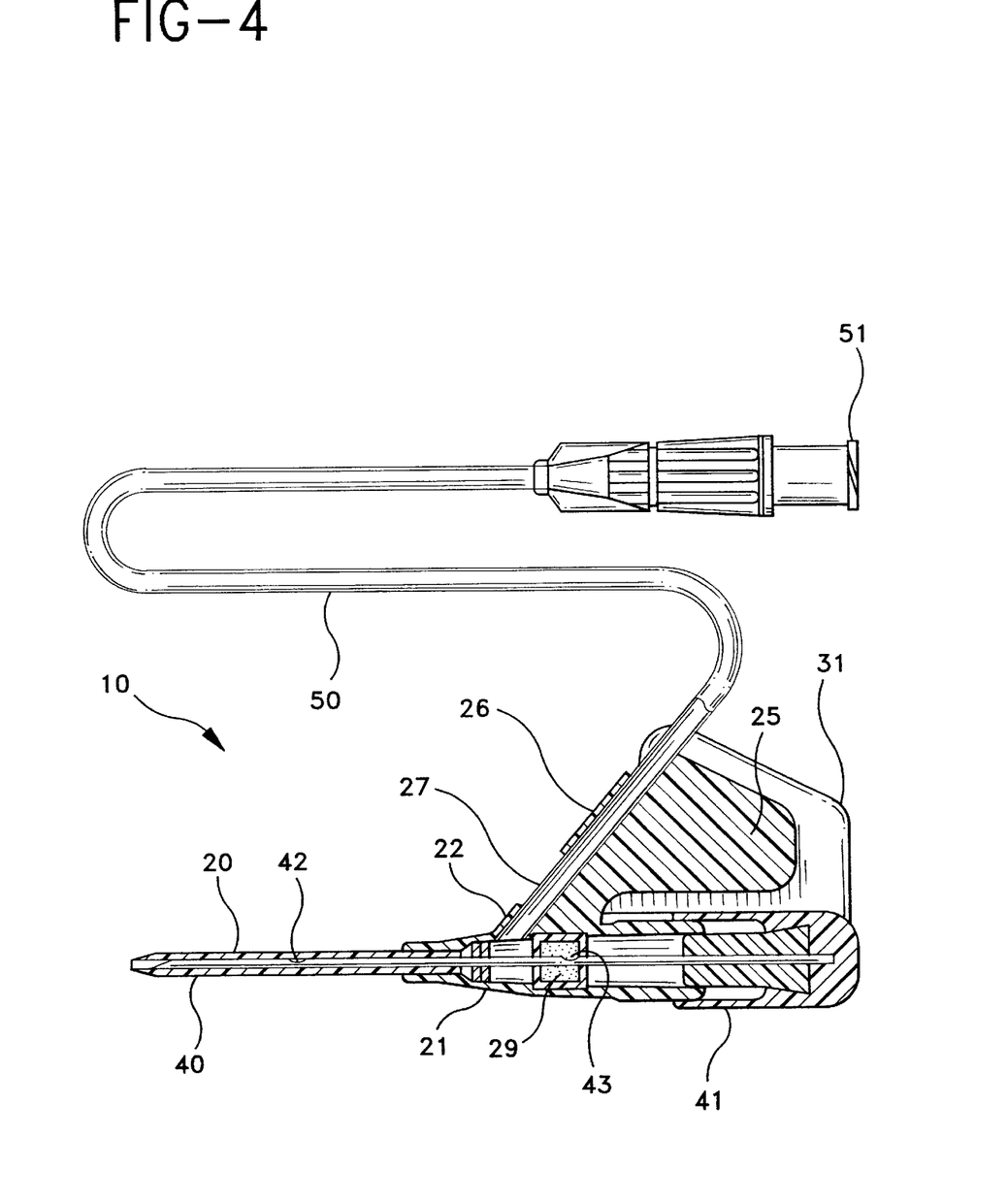
FIG. 4 is a cross-sectional view of the invention similar to the view of FIG. 2 after the distal tip of the needle has been retracted into the catheter.
Figure 5:
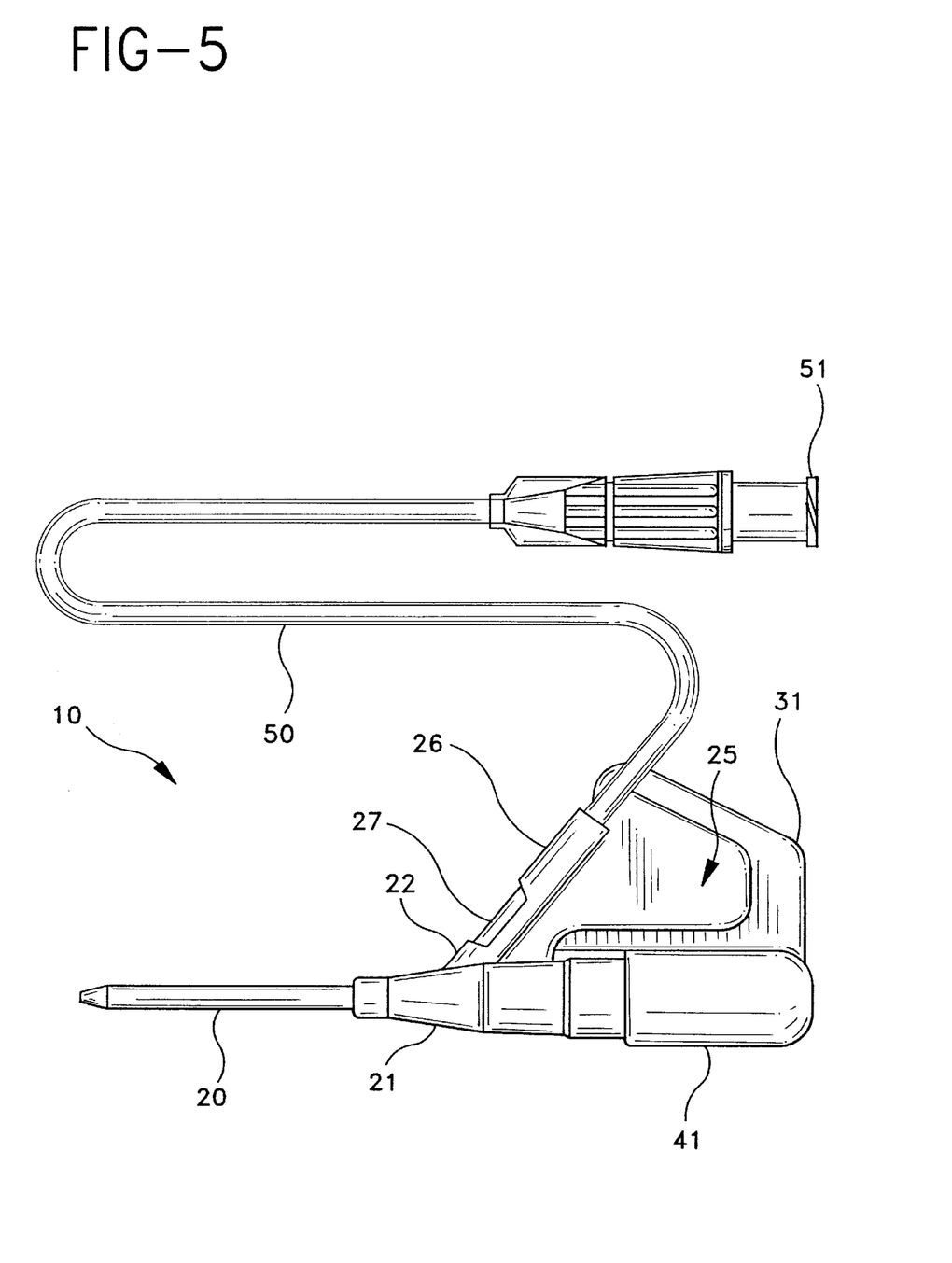
FIG. 5 is a left side elevation view of the invention after the distal tip of the needle has; been retracted.
Figure 6:
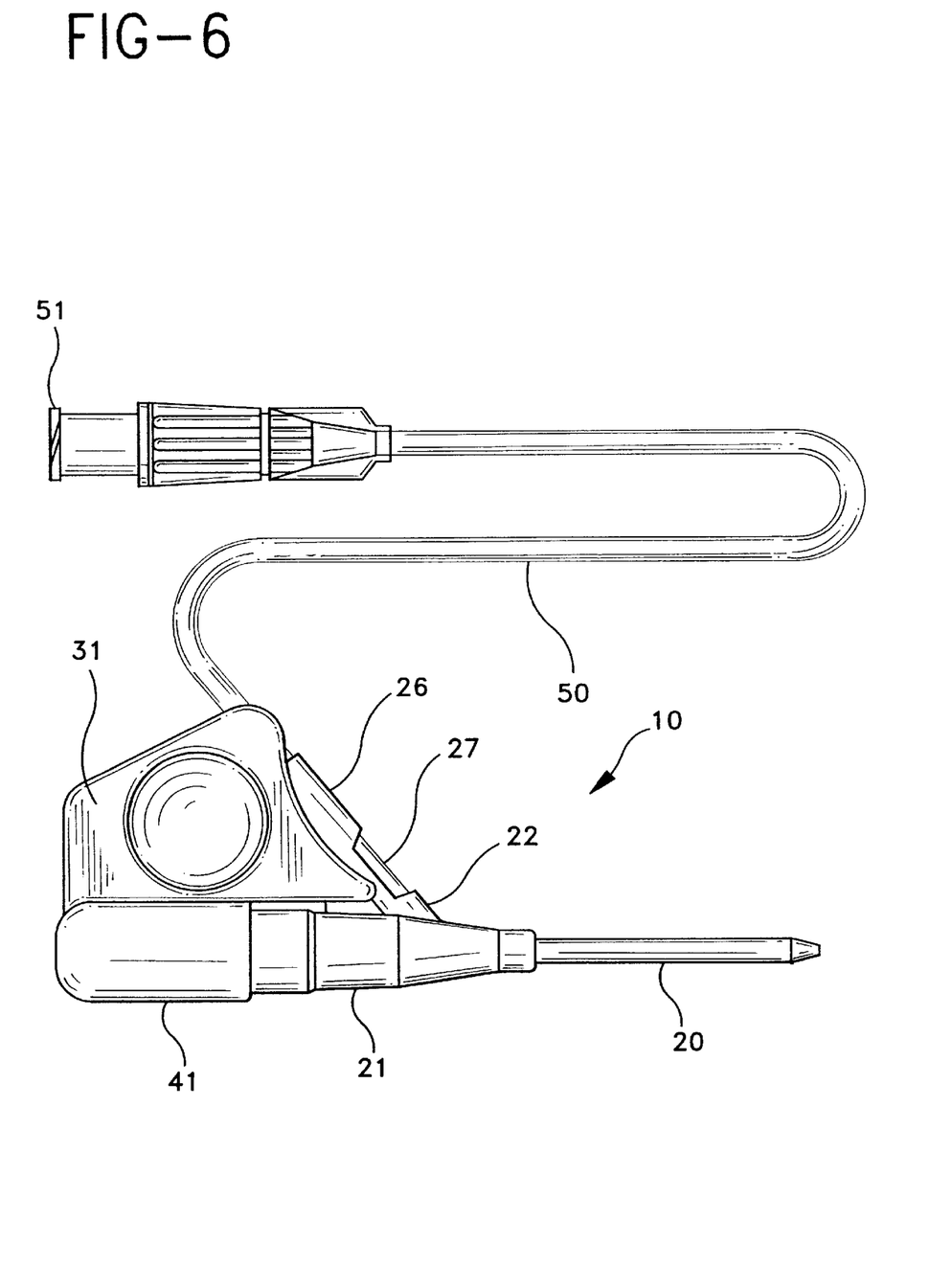
FIG. 6 is a right side elevation view of the invention showing the side opposite to the side shown in FIG. 5.
Figure 7:
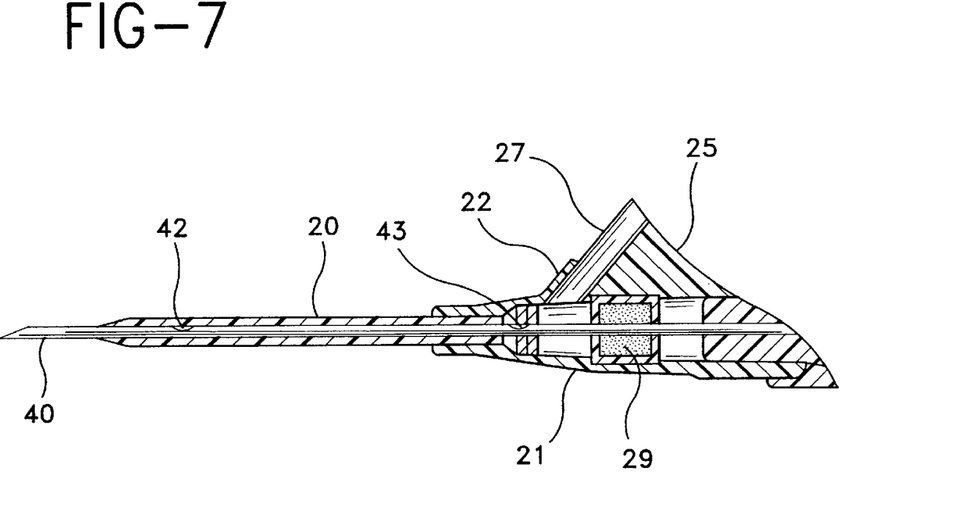
FIG. 7 is an enlarged view of the forward portion of the invention shown in FIG. 2.
Figure 8:
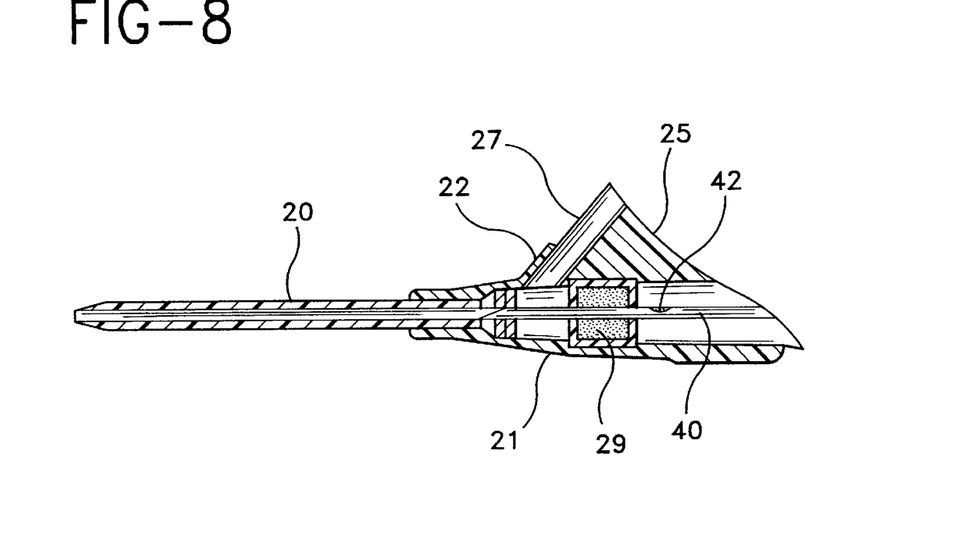
FIG. 8 is similar to the view shown in FIG. 7 but with the needle retracted.
Figure 9:
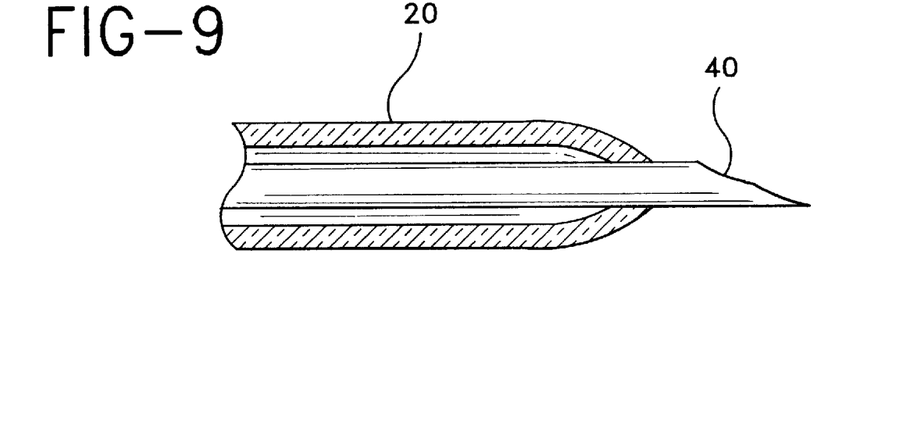
FIG. 9 is an enlarged view of the distal tip of the needle and catheter with the needle in the forward position.
Figure 10:
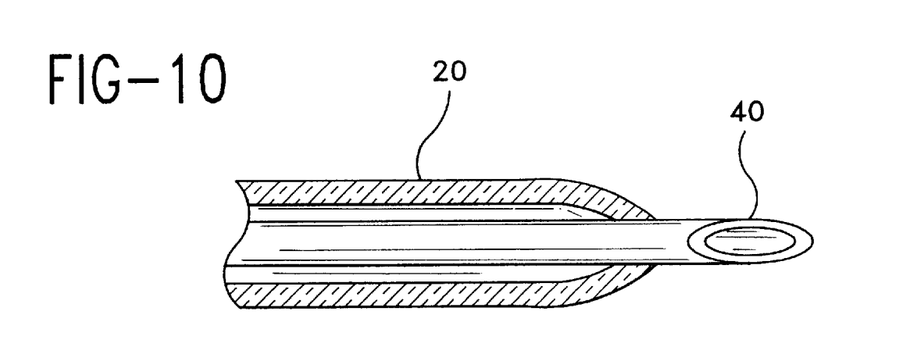
FIG. 10 is an enlarged view of the distal tip of the needle and catheter with the needle rotated with respect to the catheter.
Figure 11:
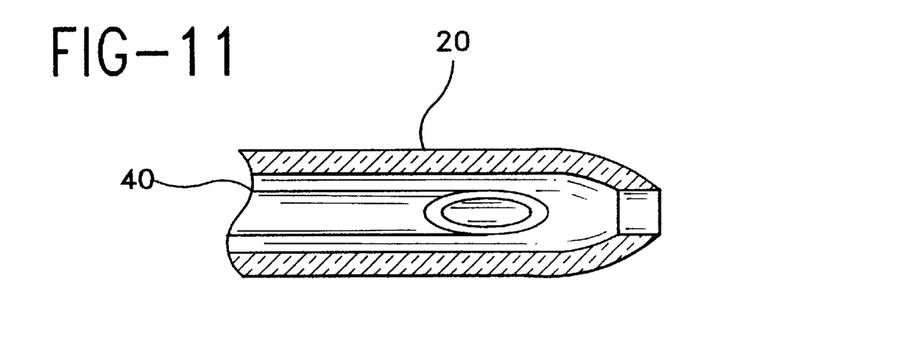
FIG. 11 is an enlarged view of the distal tip of the needle and catheter with the needle withdrawn into the catheter.

Catheter hub 21 includes a side port 22 which has an extension tube 50 connected thereto located toward the distal portion of catheter hub 21. The proximal end of extension tube 50 includes a standard luer lock adaptor 51 to allow the connection of an IV fluid supply line to extension tube 50. Such an IV fluid supply line can be connected to extension tube 50 prior to insertion of assembly 10 into a patient. Side port 22 is in fluid communication with the lumen of catheter 20 so that fluid infused through extension tube 50 will pass into the patient once catheter 20 is properly positioned in the patient. Conversely, blood exiting a patient's vein through catheter 20 can travel through extension in 50. The proximal end of catheter hub 21 is sealed with an elastomeric plug 29, such as silicone, (See FIGS. 2 and 4) to ensure that fluid does not leak out of the proximal end of catheter hub 21. Catheter hub 21 also includes a wing 25 that extends radially from catheter hub 21. Wing 25 is generally aligned with the longitudinal axis of catheter 20. Wing 25 should be large enough to be grasped easily by a healthcare worker.

The forward or distal end of wing 25 defines a tubular member 26. Preferably tubular member 26 does not extend the full length of the distal end of wing 25. Extension tube 50 fits through tubular member 26 and into communication with side port 22. The space between side port 22 and tubular member 26 defines a window 27 that allows the healthcare worker to observe the distal portion of extension tube 50. At least that part of extension tube 50 that extends past window 27 is formed from polyvinyl chloride so that it is translucent or transparent in window 27. In this manner, flashback of blood can be observed in window 27 once needle 40 has entered a patient's vein. Window 27 is not necessary where tubular member 26 is made of a clear material such as polycarbonate. In such a case, flashback of blood through extension tube 50 can be seen through tubular member 26.

Needle 40 has its proximal end connected to needle hub 41. Radially extending fin 31 is formed on needle hub 41 and is generally longitudinally aligned with needle 40. Needle 40 includes a pair of notches 42 and 43 formed therein. One notch 42 is preferably located adjacent to the distal tip, while the other notch 43 is positioned on needle 40 such that when needle 40 is inserted into catheter 20 in the fully forward position, see FIG. 2, notch 43 is distal of elastomeric plug 29 and is in fluid communication with extension tube 50. Notch 42 is preferably located within about ½ inch of the heel of the needle. Notch 43 is preferably located within ½ inch of side port 22.

Figure 2:
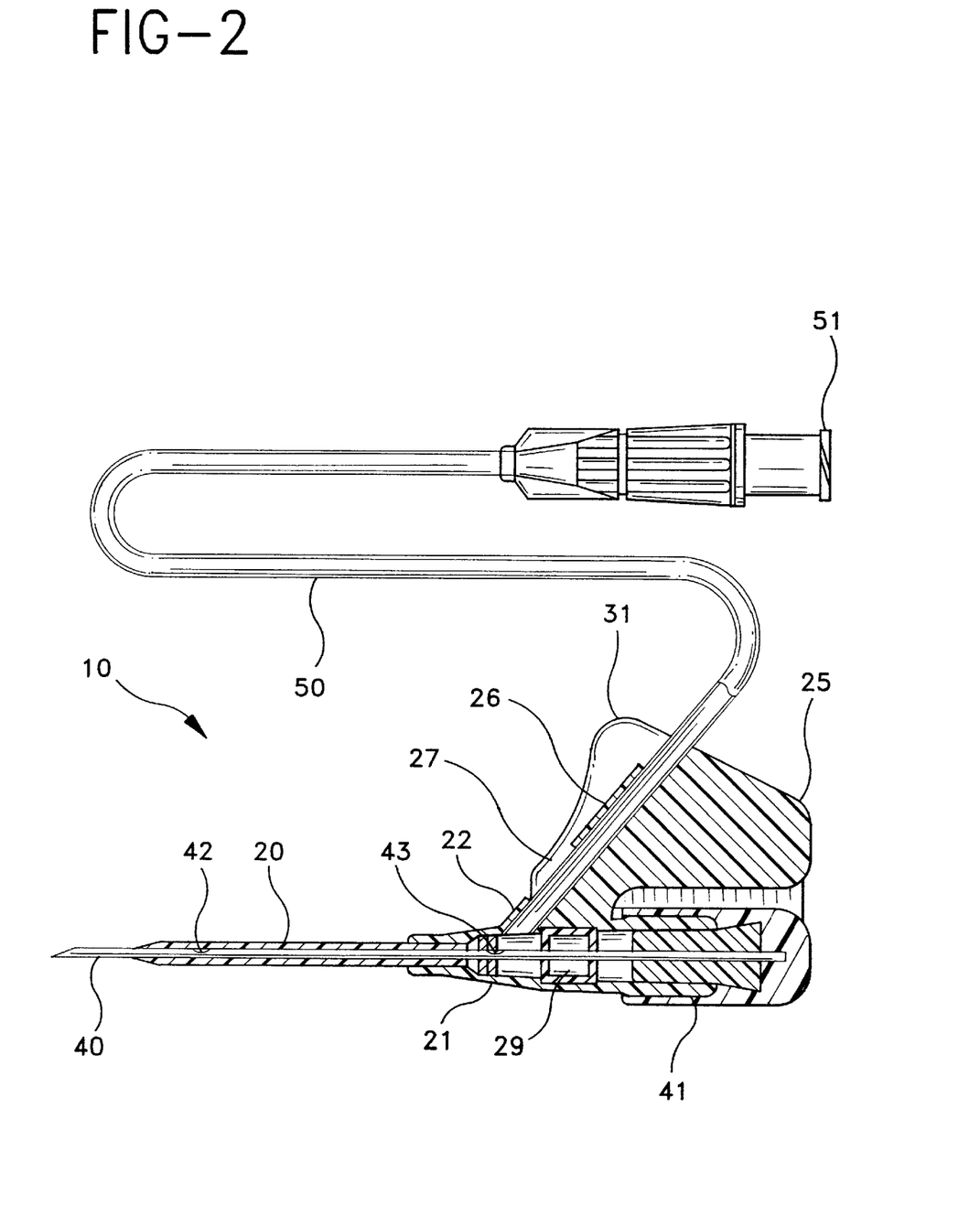
FIG. 2 is a cross-sectional view of the invention taken along line 2—2 in FIG. 1 showing the assembly prior to insertion into a patient with the needle in the forward position.
Figure 3:
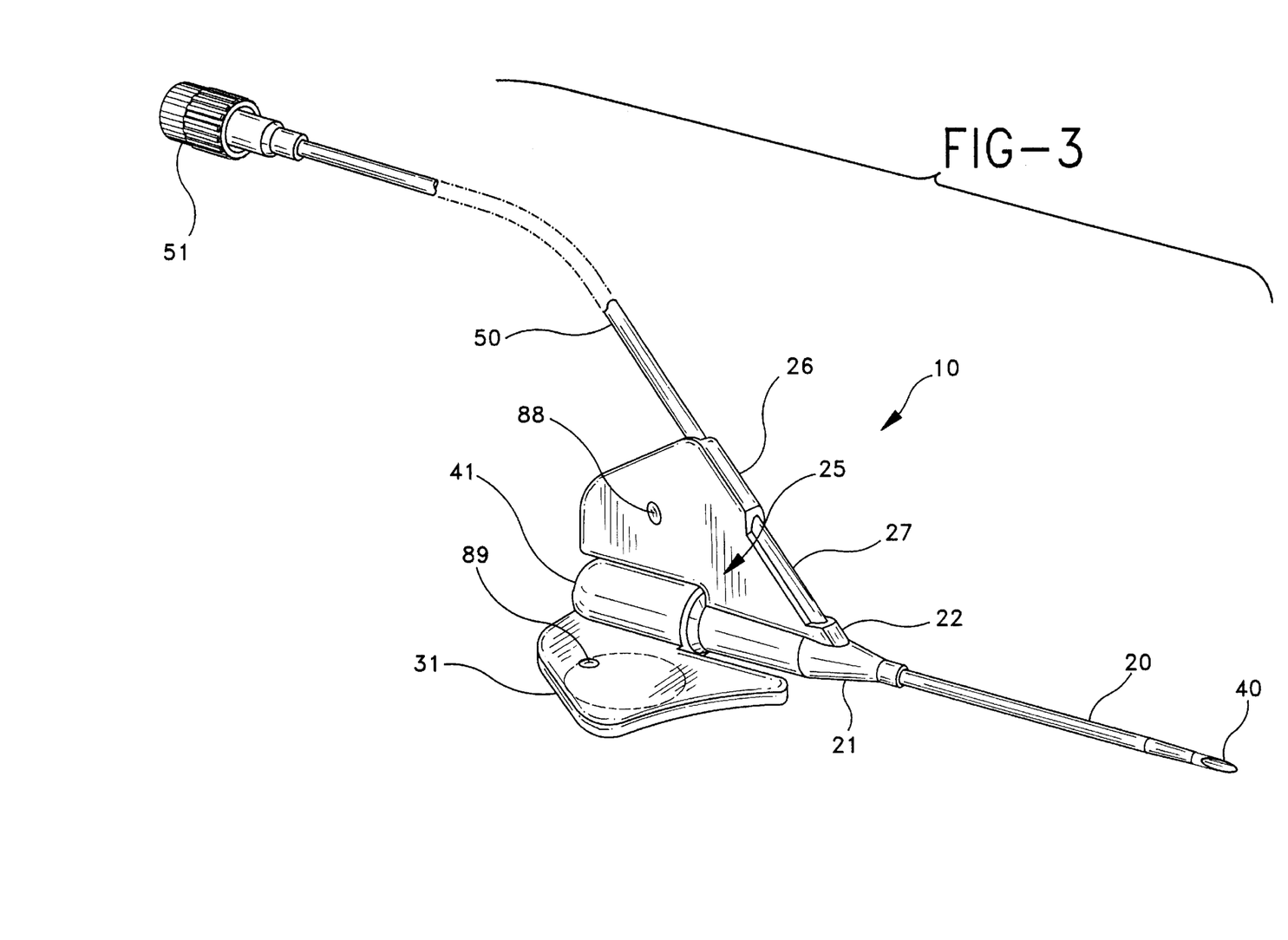
FIG. 3 is a right perspective view of this invention showing the rotation of the needle with respect to the catheter.

When needle 40 is inserted completely into catheter 20 in the forward most position so that needle hub 41 is engaged with catheter hub 21, the distal tip of needle 40 extends beyond the distal tip of catheter 20 as shown in FIG. 2. In addition, the distal end of fin 31 extends beyond the distal end of wing 25 as shown in FIG. 2. In this arrangement and with fin 31 adjacent to wing 25, catheter and introducer needle assembly 10 is ready for insertion into a patient. The healthcare worker grips both wing 25 and fin 31 to insert catheter and introducer needle assembly 10 into a patient. Because wing 25 and fin 31 are close to the distal tip of needle 40, insertion of catheter and introducer needle assembly 10 into a patient is relatively simple and the healthcare worker can control catheter and introducer assembly 10 much easier than with prior catheter and needle assemblies. The outer surface of fin 31 and wing 25 may each be formed with an impression therein to making it even easier for the healthcare worker to grasp fin 31 and wing 25. In addition, the inner surface of wing 25 may have a bump 88 that mates with a notch 89 formed on the inner surface of fin 31. The bump 88 and notch 89 are positioned in such a way that they align fin 31 forward of wing 25 so that the distal tip of needle 40 extends beyond the distal tip of catheter 20. Of course, bump 88 could be formed on fin 31 while mating notch 89 could be formed on wing 25. Prior to insertion of catheter and introducer needle assembly 10 into a patient, fin 31 and wing 25 can be rotated away from each other, see FIG. 3, to thereby cause rotation of needle 40 with respect to catheter 20 and break any adhesion therebetween.

After catheter and introducer needle assembly 10 has been inserted into a vein, flashback of blood in needle 40 will be observed through notch 42 if catheter 20 is transparent or translucent. In addition, flashback of blood will be observed through the part of extension tube 50 that is in window 27 as long as at least this portion of extension tube 50 is transparent or translucent. Flashback of blood will be observed in window 27 because blood will exit notch 43 and travel up extension tube 50 past window 27. At this point, the healthcare worker can simply push the distal end of fin 31 in the proximal direction to shield the distal tip of needle 40 inside catheter 20. See FIGS. 4, 5, 6, 8 and 11. By shielding the distal tip of needle 40 inside catheter 20, catheter 20 can be advanced into the vein without needle 40 puncturing the vein again. Needle 40 provides column strength to catheter 20 as it is advanced into the vein. Needle 40 can then be removed from catheter hub 21 leaving catheter 20 in place in the patient.

Plug 29 may be filled with gel, such as silicone gel. This gel would seal the hole left by needle 40 when it is removed from catheter hub 21. In addition, this gel would fill notches 42 and 43 when needle 40 passes through plug 29. This would prevent fluid from leaking through notches 42 and 43 while needle 40 is being removed from catheter hub 21.

Thus, it is seen that an IV catheter and introducer needle assembly is provided that is easy to control and insert into the patient, that allows adhesion between the IV catheter and the introducer needle to be broken prior to insertion of the assembly into a patient, that allows the healthcare worker to determine if the assembly is properly placed in a patient's vein without the need for the healthcare worker to divert his attention away from the insertion site, that allows an IV fluid supply line to be connected to the catheter prior to insertion of the assembly into a patient and that allows the healthcare worker to withdraw the needle into the catheter by using only one hand.

I claim:

1. A catheter and introducer needle assembly, comprising:

a catheter having a proximal end and a distal end;

a catheter hub in fluid communication with the catheter and having a proximal end and a distal end connected to the proximal end of the catheter and a side port in fluid communication with the catheter hub;

an introducer needle having a proximal end and a distal end and having a needle hub having a distal end and a proximal end, said proximal end of said introducer needle extending from the distal end of said needle hub, said introducer needle adapted to be positioned within said catheter in an insertion position wherein said distal end of said introducer needle extends distally past the distal end of said catheter, said needle hub being rotatable with respect to said catheter hub and being movable proximally with respect thereto when in said insertion position;

a seal affixed to the catheter hub and located proximal of the side port, said seal sealing said proximal end of said catheter hub;

said introducer needle having an opening at said distal end and having a notch located adjacent said side port in said catheter hub when said introducer needle is in said insertion position such that fluid can communicate between said opening at said distal end of said introducer needle and said side port but is prevented from passing out of said proximal end of said catheter hub by said seal.

* * * * *